United States Patent [19]
Wood et al.

[11] Patent Number: 6,004,937
[45] Date of Patent: Dec. 21, 1999

[54] USE OF FOLLISTATIN TO MODULATE GROWTH AND DIFFERENTIATION FACTOR 8 [GDF-8] AND BONE MORPHOGENIC PROTEIN 11 [BMP-11]

[75] Inventors: Clive R. Wood, Boston; Lori Jo Fitz, Arlington, both of Mass.

[73] Assignee: Genetics Institute, Inc., Cambridge, Mass.

[21] Appl. No.: 09/037,118

[22] Filed: Mar. 9, 1998

[51] Int. Cl.$^6$ ............................ A61K 38/00; A61K 38/16
[52] U.S. Cl. ................................. 514/21; 514/8; 514/21; 435/325; 435/69.1; 435/69.4; 435/320.1; 435/172.3; 435/252.3; 530/350; 530/397; 530/399; 536/23.1; 536/23.5; 536/23.51; 536/24.33
[58] Field of Search ................................. 514/8, 21, 12; 435/325, 69.1, 69.4, 320.1, 172.3, 252.3; 530/350, 397, 399; 536/23.1, 23.5, 23.51, 24.33

[56] References Cited

U.S. PATENT DOCUMENTS

| | | | |
|---|---|---|---|
| 5,041,538 | 8/1991 | Ling et al. | 530/395 |
| 5,171,579 | 12/1992 | Ron et al. | 424/486 |
| 5,545,616 | 8/1996 | Woodruff | 514/12 |
| 5,827,733 | 10/1998 | Lee et al. | 435/325 |

FOREIGN PATENT DOCUMENTS

| | | |
|---|---|---|
| 9675056 | 11/1996 | Australia . |

OTHER PUBLICATIONS

Massague, *Cell,* 69:1067–1070 (1992).
Attisano et al., *Cell 68*:97–108 (1992).
Lin et al., *Cell,* 68:775–785 (1992).
Wang et al., *Cell 67*:797–805 (1991).
Mathews et al., *Cell 65*:973–982 (1991).
Nakamura et al., *J.Biol. Chem.* 267:18924–18928 (1992).
Ebner et al., *Science*, 260:1344–1348 (1993).
Sugino et al., *J.Biol. Chem.*268:15579(1993).
Sumitomo et al., *Biochem. Biophys. Acta* 208:1(1995).
Nakamura et al., *J. Biol. Chem.* 266:19432 (1991).
Inouye et al., *Mol Cell. Endocrinol.* 90:1(1992).
Shimasaki et al., *PNAS:USA* 85:4218–4222 (1988).
Ueno et al., *PNAS:USA* 84:8282–8286 (1987).
Robertson et al., *Biochem. Biophys. Res. Commun.* 149:744–749 (1987).
T. Maniatis et al., i Molecular Cloning (A Laboratory Manual), Cold Spring Harbor Laboratory (1982), pp. 387 to 389.
A. Fainsod et al., "The dorsalizing and neural inducing gene follistatin is an antagonist of BMP–4" *Elsevier Science Ireland Ltd. Mechanism of Development,* pp. 39–50, (63), 1997.

*Primary Examiner*—F. T. Moezie
*Attorney, Agent, or Firm*—Steven R. Lazar

[57] ABSTRACT

Methods are provided for the modulation of the effects of GDF-8 and BMP-11, particularly on neural and muscular disorders administration of follistatin for treating neural, muscle, disorders which are characterized by an abnormality in the levels or activity of GDF-8 or BMP-11.

9 Claims, No Drawings

USE OF FOLLISTATIN TO MODULATE GROWTH AND DIFFERENTIATION FACTOR 8 [GDF-8] AND BONE MORPHOGENIC PROTEIN 11 [BMP-11]

FIELD OF THE INVENTION

The present invention relates to use of follistatin to modulate the activity of a growth and differentiation factor [GDF] known as GDF-8. More particularly, the invention relates to use of follistatin for treating neural and muscle, disorders which are related to modulation of the levels or activity of GDF-8 or closely related factors, including bone morphogenetic protein-11 [BMP-11], also known as GDF-11.

BACKGROUND OF THE INVENTION

Bone morphogenetic proteins (BMPs) and growth/differentiation factors (GDFs) are part of a family of proteins which have been identified as having the ability to induce the growth, formation, differentiation and maintenance of various tissues, including bone, cartilage, tendon/ligament, muscle, neural, and various organs. BMPs and GDFs are subfamilies within the TGF-β superfamily.

The TGF-β superfamily of proteins have been shown to bind to serine/threonine kinase receptors. Massague, *Cell* 69:1067–1070 (1992); Attisano et al., *Cell* 68:97–108 (1992); Lin et al., *Cell* 68:775–785 (1992); Wang, et al., *Cell* 67:797–805 (1991). Similarly, activin receptors have been isolated and characterized as a predicted transmembrane serine kinase. Mathews et al., *Cell* 65:973–982 (1991); Nakamura et al., *J. Biol. Chem.* 267:18924–18928 (1992). Ebner et al., *Science,* 260:1344–1348 (1993) describe the existence of Type I and Type II TGF-β receptors, and the effects of the Type I receptor on binding of TGF-β to the Type II receptor.

Follistatin is a protein which has been identified as a molecule which is able to bind to activin, another member of the TGF-β superfamily, and as a possible antagonist of activin. U.S. Pat. No. 5,545,616. Accordingly, follistatin has been suggested for possible use to predict and/or prevent preterm labor and to suppress FSH secretion from the pituitary [U.S. Pat. No. 5,545,616]; to have inhibin like activity [U.S. Pat. No. 5,041,538]; and for use in rheumatoid arthritis [AU9675056, Kaneka Corp].

SUMMARY OF THE INVENTION

Accordingly, the present invention provides methods for modulating the effects on cells of a protein selected from the group consisting of growth and differentiation factor 8 [GDF-8] and bone morphogenetic protein 11 [BMP-11], said method comprising administering to said cells an effective amount of follistatin. The invention further provides methods for blocking the effects on cells of GDF-8 or BMP-11 and methods for treating a disorder associated with neural or muscular effects of GDF-8 or BMP-11, said method comprising administering to said cells an effective amount of follistatin.

In one embodiment, the present invention comprises methods of modulating the production and/or activity of GDF-8 or BMP-11, thereby affecting the growth, formation, differentiation and maintenance of cells using a follistatin protein, or a DNA molecule encoding a follistatin protein. The present invention further comprises treatment of disorders which are associated with the production, metabolism and activity of GDF-8 or BMP-11. Preferred embodiments include treatment of diseases and disorders involving neural or neuronal and muscle cells and tissue. These disorders include neurodegenerative and musculodegenerative diseases, such as muscle or nerve wasting, muscle or nerve atrophy, amyotrophic lateral sclerosis, Alzheimer's Disease, Parkinson's Disease and muscular dystrophy. The present invention further includes the use of follistatin for the treatment of traumatic or chronic injury to the spinal cord, or to the nerve or muscle system.

DETAILED DESCRIPTION OF THE INVENTION

TGF-β protein, such as BMPs and GDFs, are characterized by their ability to promote, stimulate or otherwise induce the growth, formation, differentiation and maintenance of various tissues, including bone, cartilage, tendon/ligament, muscle, neural, and various organs. GDF-8 has been shown to exhibit particular activity on muscle, adipocyte and neural tissue. BMP-11 has been shown to exhibit activity on neural cells, particularly on neuronal cells.

Two forms of follistatin (FS) are produced as a result of alternative splicing. These forms are FS-288 and FS-315. The FS-315 form has also been shown to be proteolytically processed to form FS-303 (Sugino et al., *J. Biol. Chem.* 268:15579(1993)). Recombinant forms of each of these molecules are expected to have different properties (Sumitomo et al., *Biochem. Biophys. Acta* 208:1(1995)) and are envisaged to be useful for inhibiting the action of GDF-8 and BMP-11.

The expected properties of follistatin, in light of the present showing, include differential ability to interact with cell surfaces, and bind heparin and heparin sulphate proteoglycans (Nakamura et al., *J. Biol. Chem.* 266:19432 (1991); Sumitomo et al., *Biochem Biophys. Acta* 208:1 (1995)). These properties may be suboptimal in the FS used for therapeutic use. As a consequence, site-directed mutagenesis may be used to alter this property. Specifically, this can involve changing or deleting the basic residues responsible for heparin binding, at residues 72–86 (Inouye et al., *Mol Cell. Endocrinol.* 90:1(1992)).

Follistatin is useful, among other uses, for the identification of BMPs, the identification of further BMP receptors, and the identification of ligands or molecules, including antibodies, which are able to mimic the binding characteristics of BMPs. These ligands may act as agonists or antagonists, depending upon the individual ligand. The ability of follistatin to block or modulate the activity of GDF-8 and BMP-11 may be characterized in an assay for BMP activity, such as the animal cap assay, described at Example 2 below. The follistatin molecules are also useful in inhibiting the effects of GDF-8 and BMP-11, where such inhibition is desired.

Because of the known activities of GDF-8 and BMP-11, the present invention will find use in treating muscle-related disorders, diseases of the nervous system (including infections), vascular disorders, trauma, metabolic derangements, demyelinating diseases (including multiple sclerosis), neuronal diseases (including Alzheimer's disease, Parkinson's disease and Huntington's chorea; and including motor neuron diseases such as amyotrophic lateral sclerosis, primary lateral sclerosis and Werdnig-Hoffmann disease), epilepsy, syringomyelia, peripheral neuropathy, congenital anomalies and tumors. Muscle-related conditions for treatment include without limitation muscular dystrophies (such as severe and benign X-linked muscular dystrophy, limb-girdle dystrophy, facioscapulohumeral dystrophy, myotinic dystrophy, distal muscular dystrophy, progressive dystrophic ophthalmoplegia, oculopharyngeal dystrophy and Fukuyama-type congenital muscular dystrophy), congenital myopathy, myotonia congenital, familial periodic paralysis, paroxysmal myoglobinuria, myasthenia gravis, Eaton-Lambert syndrome, secondary myasthenia, denervation atrophy.

Follistatin proteins useful in the present invention include human follistatin, disclosed in Shimasaki et al., *PNAS:USA* 85:4218–4222 (1988); porcine follistatin, disclosed in Ueno et al., *PNAS:USA* 84:8282–8286 (1987); and bovine follistatin, disclosed in Robertson et al., *Biochem. Biophys. Res. Commun.* 149:744–749 (1987). The disclosures of each of these publications is hereby incorporated by reference herein. In addition, truncated polypeptides which comprise partial fragments of the full follistatin polypeptides, and which retain the ability to bind to GDF-8 and BMP-11, may also be useful for the present invention. In particular, functional fragments of follistatin sequences, which maintain the ability to modulate, block or otherwise affect GDF-8 and/or BMP-11 activity, are useful for the methods of the present invention. The identification of a partial follistatin polypeptide as a functional fragment of follistatin may readily be determined, for example, using the assay described in Example 2.

The present invention also includes fusions of follistatin with other molecules. This includes the fusion of FS-288, FS-315 or FS-303 sequences with the hinge, CH2 and CH3 domains of a human immunoglobulin gamma isotype, e.g., gamma 1 or 4. Such a fusion protein is expected to produce a dimeric molecule, with the improved pharmacokinetics expected for an immunoglobulin Fc fusion. In addition, the constant domains or secretory tailpieces of alpha or mu immunoglobulin heavy chains may be fused to FS in order to generate polymeric forms of FS.

The component portion of FS responsible for interacting with GDF-8 and BMP-11 can be identified and used to generate functional fragments of FS, fusion proteins, or as the basis for other therapeutic utilities. The human FS gene contains four domains each encoded on a separate exon, in addition to an exon encoding a N-terminal signal sequence, and an exon encoding the C-terminal extension that results in FS-315 (Shimasaki et al., *Proc. Natl. Acad. Sci USA* 85:4218(1995)). The regions responsible for GDF-8 and/or BMP-11 binding can be determined and prepared by the methods described in Example 3.

For use in the methods of the present invention, the purified follistatin proteins and functional fragments thereof may be produced through purification from native tissues, or recombinantly by culturing a host cell transformed with a DNA sequence comprising the DNA coding sequence described in any of the above publications. In addition to the native DNA coding sequences, coding sequences which can be used include sequences which code for the above, but which differ in codon sequence due to the degeneracies of the genetic code or allelic variations (naturally-occurring base changes in the species population which may or may not result in an amino acid change), as well as DNA sequences which hybridize under stringent hybridization conditions [see, T. Maniatis et al, *Molecular Cloning (A Laboratory Manual)*, Cold Spring Harbor Laboratory (1982), pages 387 to 389] to the DNA sequences described in the above publications and encode a protein having the ability to bind to GDF-8 or BMP-11. Variations in the DNA sequences disclosed in the above publications which are caused by point mutations or by induced modifications (including insertion, deletion, and substitution) to enhance the activity, half-life or production of the follistatin polypeptides encoded thereby are also useful for the present invention.

The present invention may include gene therapy, in which transfection of cells' with DNA molecules encoding follistatin or functional fragments thereof is made in order to achieve binding of the follistatin to GDF-8 and/or BMP-11 present within the transfected cells or in the environment of the transfected cells, and thereby modulate or block the effects of GDF-8 and/or BMP-11 on those cells. For example, cells which express the follistatin proteins may reduce or eliminate the effects of an excess of GDF-8 or BMP-11 in an organism or cell. The increased follistatin may be desirable for minimizing negative effects of GDF-8 or BMP-11, or may act as a complex with GDF-8 or BMP-11 to enhance or increase activity.

Follistatin proteins or functional fragments thereof may also be useful in au process for isolating GDF-8 or BMP-11 in a purification process. In such a process, follistatin may be incorporated into a column or a resin which may be used for the commercial production of GDF-8 or BMP-11 from tissue samples or via recombinant processes. The follistatin or functional fragments thereof are used to bind to the GDF-8 or BMP-11, and later subjected to conditions which result in the release of said bound protein.

The present invention includes therapeutic methods comprising administering a follistatin containing composition topically, systematically, or locally as an implant or device. When administered, the therapeutic composition for use in this invention is preferably in a pyrogen-free, physiologically acceptable form. Further, the composition may desirably be encapsulated or injected in a viscous form for delivery to the desired site. Therapeutically useful agents, such as growth factors (e.g., BMPs, TGF-$\beta$, FGF, IGF), cytokines (e.g., interleukins and CSFs) and antibiotics, may also optionally be included in or administered simultaneously or sequentially with, the Follistatin composition in the methods of the invention.

There is a wide range of methods which can be used to deliver the cells expressing follistatin proteins to a site for use in modulating a GDF-8 or BMP-11 response. In one embodiment of the invention, the cells expressing follistatin protein can be delivered by direct application, for example, direct injection of a sample of such cells into the site of tissue damage. In a particular embodiment, these cells can be purified. In a preferred embodiment, the cells expressing follistatin protein can be delivered in a medium or matrix which partially impedes their mobility so as to localize the cells to a site of injury. Such a medium or matrix could be semi-solid, such as a paste or gel, including a gel-like polymer. Alternatively, the medium or matrix could be in the form of a solid, preferably, a porous solid which will allow the migration of cells into the solid matrix, and hold them there while allowing proliferation of the cells.

In a method of the present invention, the cells expressing follistatin are applied in the desired site as described above, and GDF-8 or BMP-11 is applied. The factor may be applied simultaneously or immediately following application of the cells expressing follistatin. The BMP may be applied in manners known in the art, such as described in the above patents, as well as in U.S. Pat. No. 5,171,579, the disclosure of which is also hereby incorporated by reference.

Expression of Follistatin Protein

In order to produce follistatin protein, the DNA encoding the desired protein is transferred into an appropriate expression vector and introduced into mammalian cells or other preferred eukaryotic or prokaryotic hosts by conventional genetic engineering techniques. The presently preferred expression system for biologically active recombinant follistatin protein is stably transformed mammalian cells.

The following examples detail presently preferred embodiments of the present invention. Numerous modifications and variations in practice thereof are expected to occur to those skilled in the art upon consideration of these descriptions. Those modifications and variations are believed to be encompassed within the claims appended hereto. The examples do not in any way limit the invention.

EXAMPLES

Example 1

BIAcore Binding Assay

Purified follistatin was coupled to a carboxymethyl dextran layer of a CM5 research grade chip on a Biacore 2000 instrument using standard amine coupling procedures according to the manufacturer's instructions. The buffer used for immobilization was 10 mM sodium acetate pH 4. Typically about 7,000 response units (RU) of follistatin were immobilized by this procedure. Purified BMP and GDF proteins were each injected over the immobilized follistatin for 10 minutes at 2 µl/min. The running buffer used for screening was 10 mM sodium phosphate pH 7.4, 300 mM sodium chloride, 3.4 mM ethylenediaminetetra-acetic acid, 0.005% (v/v) Tween 20 and the temperature was maintained at 22° C. Binding was quantified as an increase in RU at 60 sec after the end of the injection compared to a baseline established 20 sec prior to injection. Specific binding was shown by coinjection of soluble follistatin and the BMP-11 and GDF-8 proteins.

Results

Results from the Biacore screen showed that both GDF-8 and BMP-11 bound follistatin. This binding was comparable to the positive control, activin. The binding was specific, as demonstrated by the fact that no binding was observed when GDF-8 or BMP-11 was preincubated and coinjected with excess soluble follistatin.

Example 2

Animal Cap Assay Method

The Xenopus animal cap assay has been used to assess the biological activity of BMP proteins. Xenopus eggs were fertilized in vitro and allowed to develop until the blastula stage. The ectodermal or animal cap of the embryo was excised and cultured in media containing the protein of interest for 5–6 hours. The explants were then transferred to fresh media without protein. The animal caps were cultured overnight and the activity of the protein was evaluated the next day by morphology, histology, and RT-PCR using molecular markers of mesoderm, neural tissue, and endoderm.

Animal Cap Assay Results

Both GDF-8 and BMP-11 caused animal caps to elongate and induced dorsal mesoderm (muscle) and neural tissue at doses (50 ng/ml) comparable to that for factors that have been shown previously to induce these tissues (e.g., activin). Follistatin was able to inhibit the ability of both GDF-8 and BMP-11 to induce elongation and mesodermal tissue in animal caps. GDF-8 was blocked by a 5 fold excess of follistatin (100 ng/ml GDF-8 and 500 ng/ml follistatin) while BMP-11 was blocked by a 10 fold excess of follistatin (BMP-11 50 ng/ml and 500 ng/ml follistatin). Together, the Biacore binding results and inhibition on the Xenopus animal cap assay demonstrate that follistatin is an antagonist of GDF-8 and BMP-11, and is able to modulate the activity of these two factors.

Example 3

Determination of Functional Fragments of Follistatin

Functional fragments of Follistatin, and the components of Follistatin that are necessary for the preparation thereof, are defined by generating a series of FS mutants each with an additional exon deleted from the 3' end. The six exons of FS are numbered 1 to 6. The mutants will consist of exons 1–5, 1–4, 1–3 and 1–2 and the binding of each form will be compared with wild-type FS (1–6). This will identify the domain or domains responsible for ligand binding. Specific residues that are critical for binding to ligand will then be identified using site-directed mutagenesis.

The 1–5, 1–4, 1–3 and 1–2 forms will be generated by using oligonucleotide primers and the polymerase chain reaction (PCR). The template for this amplification will be the FS cDNA, either from a plasmid clone or as the result of random hexamer-primed first strand cDNA synthesis from primary tissue poly A+RNA (e.g., from ovary RNA). A forward (5') primer based on the start codon of FS will be used in each amplification, and combined with a reverse (3') primer that anneals to the 3' coding sequence of the final exon (e.g., exon 5 for the 1–5 form) and introduces a stop codon immediately after the final exon. Recognition sequences of restriction endonucleases will also be added to the 5' end of each primer to facilitate molecular cloning of the PCR product into an expression vector. PCR conditions and components will be chosen to minimize the introduction of point mutations, and the resulting clones will be analyzed by nucleotide sequencing to ensure the correct FS sequence is present in each construct.

The forward primer is called FS-forward. The reverse primer for generating 1–5 is called FS-reverse 5; for 1–4 is called FS-reverse 4; for 1–3 is called FS-reverse 3; and for 1–2 is called FS-reverse 2. Potential sequences for these primers are given below. The FS sequences responsible for interacting with GDF-8, BMP-11 and activin may be identical. If the binding sites are discrete or overlapping, mutagenesis can be used to abolish binding to specific FS ligands. This can be achieved by alanine-scanning mutagenesis and testing of each mutant for binding to each of the three ligands.

FS-forward: 5'-dCCAGGATGGTCCGCGCGAGG-3' [SEQ ID NO:1]

FS-reverse 5: 5'-dTCAGTTGCAAGATCCGGAGT-3' [SEQ ID NO:2]

FS-reverse 4: 5'-dTCATTTGATACACTTTCCCTCAT-3' [SEQ ID NO:3]

FS-reverse 3: 5'-dTCACTTTTTACATCTGCCTTGGT-3' [SEQ ID NO:4]

FS-reverse 2: 5'-dTCATTCTTTACAGGGGATGCAGT-3' [SEQ ID NO:5]

Using techniques and primers similar to those described above, a series of FS mutants each with an additional exon deleted from the 5' end is generated in order to determine whether the N-terminal portion of the Follistatin protein are required for functional fragments of Follistatin. These mutants will consist of exons 3–6, 4–6, 5–6 and 6, and the binding of each form will also be compared with wild-type FS (1–6). The first exon, including the signal sequence, will be included on each construct to facilitate the proper secretion of each molecule.

We claim:

1. A method for modulating the effects of a protein on cells, wherein the protein is selected from the group consisting of growth and differentiation factor 8 (GDF-8) and bone morphogenetic protein 11 (BMP-11), said method comprising administering to said cells an effective amount of follistatin.

2. The method of claim 1, wherein the protein is GDF-8.

3. The method of claim 1, wherein the protein is BMP-11.

4. A method for blocking the effects of a protein on cells, wherein the protein is selected from the group consisting of growth and differentiation factor 8 (GDF-8) and bone morphogenetic protein 11 (BMP-11), said method comprising administering to said cells an effective amount of follistatin.

5. The method of claim 4, wherein the protein is GDF-8.

6. The method of claim 4, wherein the protein is BMP-11.

7. A method for treating a subject having a disorder associated with the effects of a protein on neural, neuronal and muscle cell neural, neuronal and muscle cells and wherein the protein is selected from the group consisting of growth and differentiation factor 8 (GDF-8) and bone morphogenetic protein 11 (BMP-11), said method comprising administering to said cell an effective amount of follistatin.

8. The method of claim 7, wherein the protein is GDF-8.

9. The method of claim 7, wherein the protein is BMP-11.

\* \* \* \* \*

UNITED STATES PATENT AND TRADEMARK OFFICE
CERTIFICATE OF CORRECTION

PATENT NO. : 6,004,937
DATED : December 21, 1999
INVENTOR(S) : Clive R. Wood and Lori Jo Fitz It is certified that error appears in the above-identified patent and that said Letters Patent is hereby corrected as shown below:

<u>Column 10,</u>
Lines 13 and 14, "neural, neuronal and muscle cell neural, neuronal and muscle cells" should read -- neural, neuronal and muscle cells --.

Signed and Sealed this

Twenty-fifth Day of May, 2004

JON W. DUDAS
*Acting Director of the United States Patent and Trademark Office*

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

CCAGGATGGT CCGCGCGAGG                                    20

(2) INFORMATION FOR SEQ ID NO:2:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:2:

TCAGTTGCAA GATCCGGAGT                                    20

(2) INFORMATION FOR SEQ ID NO:3:

(i) SEQUENCE CHARACTERISTICS:
      (A) LENGTH: 23 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:3:

TCATTTGATA CACTTTCCCT CAT                                 23

(2) INFORMATION FOR SEQ ID NO:4:

(i) SEQUENCE CHARACTERISTICS:
      (A) LENGTH: 23 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:4:

TCACTTTTTA CATCTGCCTT GGT                                 23

(2) INFORMATION FOR SEQ ID NO:5:

(i) SEQUENCE CHARACTERISTICS:
      (A) LENGTH: 23 base pairs
      (B) TYPE: nucleic acid
      (C) STRANDEDNESS: single
      (D) TOPOLOGY: linear

```
    (ii) MOLECULE TYPE: DNA (genomic)

(xi) SEQUENCE DESCRIPTION: SEQ ID NO:5:

TCATTCTTTA CAGGGGATGC AGT                                              23
```